United States Patent [19]  [11] 4,185,641
Minior et al. [45] Jan. 29, 1980

[54] PRESSURE DOME

[75] Inventors: Thaddeus G. Minior, Tewksbury; Alexander Tykulsky, Carlisle, both of Mass.

[73] Assignee: Hewlett-Packard Company, Palo Alto, Calif.

[21] Appl. No.: 936,168

[22] Filed: Aug. 23, 1978

[51] Int. Cl.² .............................................. A61B 5/02
[52] U.S. Cl. ..................................... 128/675; 73/723; 128/748
[58] Field of Search ....................... 128/673, 675, 748; 73/723–728, 756

[56] References Cited

U.S. PATENT DOCUMENTS

| 3,818,765 | 6/1974 | Eriksen | 128/2.05 E X |
| 4,064,550 | 12/1977 | Dias et al. | 73/724 X |
| 4,072,056 | 2/1978 | Lee | 73/675 X |

Primary Examiner—Kyle L. Howell
Attorney, Agent, or Firm—Donald N. Timbie

[57] ABSTRACT

A pressure dome is provided with resilient tongues that engage projections on a transducer in such manner as to draw the dome and transducer together when one is rotated with respect to the other. Detent notches for the projection ensure that the force between a dome and the transducer is always the same.

2 Claims, 7 Drawing Figures

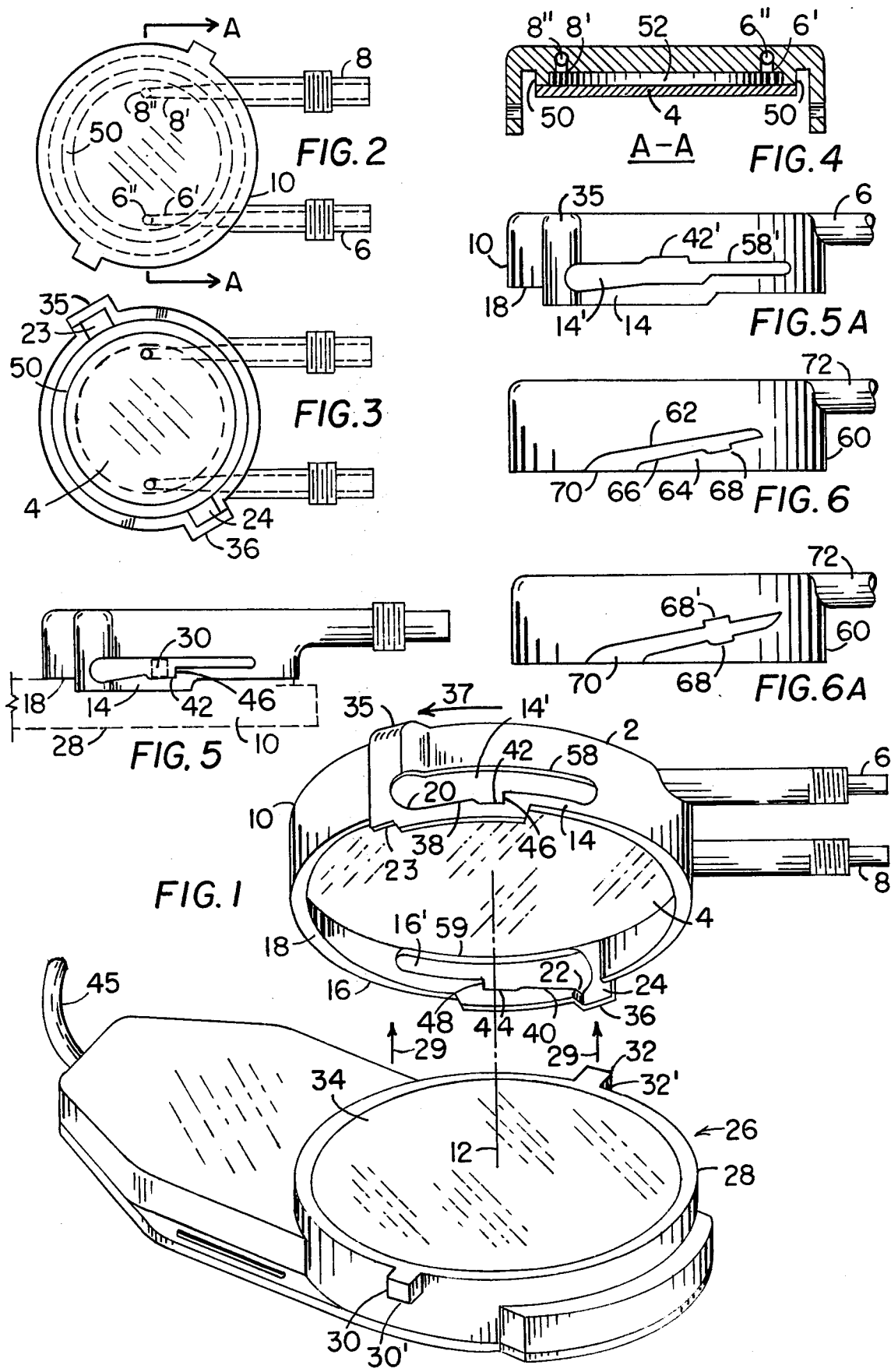

PRESSURE DOME

BACKGROUND OF THE INVENTION

In monitoring the blood pressure of a patient, it is customary to insert a catheter into an appropriate point in his circulatory system and couple the blood pressure so obtained into the hollow of a pressure dome. The hollow is closed by a flexible membrane that is maintained in intimate contact with the diaphragm of a transducer. As the blood pressure varies, the membrane moves the diaphragm of the transducer and causes corresponding variations in a blood pressure signal.

Previous pressure domes have been attached to the transducer by screw threads or other means whereby the contact pressure between the membrane of the dome and the diaphragm of the transducer depends on the applied torque. This produces a proportional offset in the blood pressure signal. If the pressure dome is attached too tightly, it may produce an offset that cannot be accommodated by the associated monitoring equipment, but, if the dome is attached too loosely, it may leak, causing errors in the blood pressure signal. Furthermore, when the pressure dome is replaced, it is usually necessary to rezero the monitoring equipment because it is unlikely that the contact pressure between the membrane of the new done and the diaphragm of the transducer will be the same as before. Variations in temperature may also alter the blood pressure signal.

BRIEF DISCUSSION OF THE INVENTION

In accordance with this invention, the pressure dome is attached to the transducer by a spring loading technique. The normal deflection of the springs is considerably larger than any variation expected because of manufacturing tolerances, and a detent is provided so that a given contact pressure is applied between the flexible membrane of the pressure dome and the diaphragm of the transducer regardless of the force used in attaching the dome to the transducer and regardless of the number of times they are assembled or disassembled. Furthermore, if any fluid pressure overload is delivered to the transducer diaphragm, the dome will overcome the force exerted by the spring and lift from the transducer so as to provide relief. Another advantage is that the springs reduce the likelihood of damage to the transducer because they act as a shock absorber.

Whereas the particular design provided herein is advantageous in any pressure dome for the reasons set forth above, it makes possible the construction of a dome of such low cost that it may be disposed of after use so as to avoid the inconvenience and expense of sterilization. Because the springs are the most vulnerable part of any such design, they are made part of the disposable pressure dome rather than part of the transducer. Furthermore, both the dome and the springs can be molded from plastic so as to reduce fabrication stresses that might otherwise develop in the spring and lead to premature failures.

One form of pressure dome embodying this invention may be briefly described as follows: A hollow with a circular periphery is formed on one side of the body of the dome. A flexible membrane is attached to the periphery so as to form an enclosed space, and ports are formed in the body so as to permit the space to be filled with fluid. Tongues that are preferably integral with the body of the dome are formed so as to lie in a cylindrical surface extending on the side of the membrane that is opposite to the hollow. Each tongue extends part way around the surface and forms a slit between it and the body of the dome. The edge of each tongue facing the membrane forms a ramp sloping toward the membrane, and detent notches are formed on one or both sides of the slit.

The transducer to which the pressure dome is to be attached is provided with projections. When they are inserted in the open ends of the slits at the free ends of the tongues, the diaphragm of the transducer is parallel to the membrane of the dome and proximate thereto. Rotation of the transducer in one direction causes its projections to ride up the ramp portions of the tongues and increase the force urging the transducer toward the dome. This forces the diaphragm of the transducer into intimate contact with the membrane of the dome. Further rotation causes the projections to drop into the detent notches, thereby determining the force applied between the membrane and the diaphragm and the value of any offset signal produced by monitoring apparatus coupled to the transducer. Shoulders are located at the sides of the detent notches that are remote from the ends of the tongues so as to prevent further rotation, but the sides of the detent notches nearer the ends of the tongues are so shaped, or they and the projections are so shaped, as to permit the rotation to be reversed and the dome to be detached from the transducer.

In a preferred embodiment, a bridge is formed between the end of each tongue and the main body of the dome. The underside of a bridge extends away from the axis of the cylindrical surface referred to so as to permit a projection on the transducer to be inserted under the bridge and into the open end of the slit formed by the tongue. This prevents the tongue from being snagged and increases the strength of the tongue.

THE DRAWINGS

FIG. 1 is a projection view of a pressure dome of the invention and a transducer for use with it, FIG. 2 is a top view of the pressure dome, FIG. 3 is a bottom view of the pressure dome, FIG. 4 is a section AA of FIG. 2, FIG. 5 is a side view of the pressure dome with a transducer attached thereto, FIG. 5A is a side view of a pressure dome in which detent notch is formed in the top edge of the slit, FIG. 6 is a side view of a pressure dome in which no bridge is provided between the end of the tongue and the body of the dome, and FIG. 6A illustrates a structure like that of FIG. 6 in which detent notches are in the upper and lower edges of the slit formed by the tongue.

In FIG. 1, the body 2 of a pressure dome is shown at such an angle as to permit a partial view of a planar circular flexible membrane 4 that covers a hollow, not shown, in the body 2 so as to form an enclosed space. Ports, not shown, within the body communicate between the enclosed space and the tubes 6 and 8 so that the space can be filled with fluid. Fluid is run into the enclosed space through one tube and out the other until air is removed and then the latter tube is closed. In this particular illustration, the body 2 includes a cylindrical rim 10 having an axis 12 that is perpendicular to the center of the membrane 4. Circumferential tongues 14 and 16 formed in the rim 10 define circumferential slits 14' and 16'. The slits 14' and 16' extend away from the membrane 4 and through the bottom edge 18 of the rim 10 at the ends 20 and 22 of the tongues 14 and 16 as indicated by the numbers 23 and 24 A transducer 26 is shown having a cylindrical body portion 28. When its axis is coaxial with the axis 12 and its outward projections 30 and 32 are aligned with the openings 23 and 24 in the dome 2, it can be moved in the direction of the arrow 29 to a position within the rim 10. In this position the planar diaphragm 34 of the transducer 26 is preferably in intimate contact with the membrane 4 of the dome 2. In the preferred form of the invention illustrated in FIG. 1, bridges 35 and 36 extend from the otherwise free ends 22 and 20 of the tongues 14 and 16, respectively, to the rim 10. It is necessary that the inner surfaces of the bridges 35 and 36, i.e., those closer to the axis 12, extend outwardly by a sufficient amount to permit the projections 30 and 32 to pass under them as they slide into the openings 23 and 24.

The height of the projections 30 and 32 along the axis 12 and the shape of their bottom surfaces 30' and 32' are such that rotation of the body 2 of the pressure dome in the direction of the arrow 37 causes the bottom surfaces 30' and 32' to ride on ramps 38 and 40 that slope from the ends of the tongues 14 and 16 toward the membrane 4. This depresses the resilient tongues 14 and 16 away from the membrane 4 and pulls it toward the diaphragm 34. Still further rotation causes the projections 30 and 32 to seat in notches 42 and 44, respectively. This sets the force between the diaphragm 34 and the membrane 4 at a given value. Manufacturing tolerances are such that the force can be nearly the same for all pressure domes so that the offset voltages produced by monitoring apparatus coupled to the transducer via electrical leads in a cable 45 are the same and rezeroing of the monitoring apparatus is not required when one pressure dome is substituted for another.

Even if more torque is applied to the dome 2 in the direction of the arrow 37 after the projections 30 and 32 are seated in the notches 42 and 44, the projections 30 and 32 bear up against the shoulders 46 and 48, respectively, so that farther rotation is prevented. Application of torque in the opposite direction, however, causes the projections 30 and 32 to ride back onto the ramps 38 and 40 and into the openings 23 and 24, thereby permitting the dome 2 to be detached from the transducer 26. This may be facilitated by curved sections that are respectively between the ramps 38 and 40 and the notches 42 and 44. Alternatively, this could be done by suitable shaping of the under surfaces 30' and 32' of the corresponding projections, or both.

FIG. 2 is a top view of the pressure dome 2 shown in FIG. 1. The inner concentric dotted circles indicate an annular ridge 50 that extends from the bottom of the dome 2, and the outer dotted circle represents the inner wall of the rim 10. The passageways in the tubes 6 and 8 extend into the dome 2, as indicated at 6' and 8', and respectively join passageways 6" and 8" that communicate with the hollow formed by the annular ridge 50. In FIG. 3, which is a bottom view of FIG. 2, the radial outward extension of the inner surfaces of the bridges 35 and 36 at the openings 23 and 24 can be readily seen. The annular ridge 50 is still dotted as it is covered by the flexible membrane 4.

FIG. 4 is a cross section of FIG. 2 taken at AA. The annular ridge 50 can be plainly seen as can the hollow 52 within the ridge. The membrane 4 is a disc of flexible plastic that is attached to the under surface of the ridge 50 by a suitable adhesive so as to make the hollow 52 into an enclosed space to which fluid pressure may be conducted via one of the ports 6' or 8' to the passageways 6" and 8" respectively. As the transducer body 28, not shown, is pressed toward the body of the pressure dome 2 by spring action described in connection with FIG. 1, the diaphragm 34 is pressed against the flexible membrane 4 and the fluid pressure in the hollow 52 is transmitted via the flexible membrane 4 to the diaphragm 34. If the pressure between the diaphragm 34 and the membrane 4 is the same regardless of what dome is used, as is the case with the structure of this invention, the offset voltage produced by monitoring apparatus will always be the same. Therefore, rezeroing the monitoring apparatus to which the transducers are electrically coupled is not necessary.

FIG. 5 illustrates the position of the tongue 14 when the projection 30 of the transducer body 28 is seated in the detent notch 42. If the tops of the projections 30 and 32 of the transducer body 28 are coplanar with the diaphragm 34, as illustrated in FIG. 1, the top edges 58 and 59 of the slits 14' and 16' should not be below the plane of the membrane 4, and the dimension of the projections 30 and 32 parallel to the axis 12 must be sufficient for their undersides to engage and depress the ramps 38 and 40 at the ends of the resilient tongues 14 and 16 respectively.

It will be apparent that the detent notches 42 and 44 could be formed in either or both of the opposing edges of the slits 14' and 16'. FIG. 5A illustrates a construction where a detent notch 42' is in the upper edge, in which case the upper edge 58' of the slit 14' will be slightly below the plane of membrane 4.

Although the bridges 35 and 36 strengthen the tongues 14 and 16 and capture their ends so as to prevent their being snagged, they can be eliminated, as indicated in FIG. 6, wherein the pressure dome has a cylindrical rim 60. A circumferential slit 62 in the rim 60 is formed by a tongue 64. The tongue 64 has a ramp 66 adjacent the free end and a detent notch 68 between the ramp 66 and the end of the root of the tongue 64 that is joined to the pressure dome. The opening 70 at the end of the tongue 64 corresponds to the openings 23 and 24 shown in FIGS. 1 and 3. A tube 72 provides access to the hollow, not shown, in the dome as previously described. FIG. 6A illustrates the same construction and designated by the same numerals as shown in FIG. 6, except for the fact that an additional detent notch 68' is formed in upper edge of the slit 62.

Although not shown in detail, instead of using a complete cylinder such as is formed by the rims 10 and 60, the circumferential tongues 14 and 16 can be formed in sections of a cylinder.

What is claimed is:

1. A pressure dome for attachment to a transducer having outwardly extending projections, comprising
a body having a hollow formed therein,
a flexible membrane,
means mounting said membrane across said hollow so as to form a space therebetween,
ports extending through said body so as to provide access to said hollow from a point outside said body, and
resilient tongues extending from said body on the side opposite said membrane from said hollow, said tongues lying within a cylinder having an axis perpendicular to said membrane and having ramps sloping toward said membrane from their ends and means defining detent notches next to said ramps.

2. A pressure dome as set forth in claim 1 having bridges extending from the ends of said tongues to said body, the surfaces of said bridges nearer said axis lying outside said cylinder.

* * * * *